United States Patent
Bossaert et al.

(10) Patent No.: US 10,738,021 B2
(45) Date of Patent: Aug. 11, 2020

(54) PREPARATION OF TMTHF

(71) Applicant: NITTO BELGIUM NV, Ghent (BE)

(72) Inventors: Greet Bossaert, Genk (BE); Charly Hoebers, Genk (BE); Bart Forier, Genk (BE); Fergal Byrne, Celbridge (IE); Andrew John Hunt, Osbaldwick (GB); Thomas James Farmer, Heslington (GB); James Hanley Clark, York (GB)

(73) Assignee: Nitto Belgium B.V., Genk (BE)

( * ) Notice: Subject to any disclaimer, the term of this patent is extended or adjusted under 35 U.S.C. 154(b) by 0 days.

(21) Appl. No.: 16/325,774

(22) PCT Filed: Aug. 18, 2017

(86) PCT No.: PCT/EP2017/070961
§ 371 (c)(1),
(2) Date: Feb. 15, 2019

(87) PCT Pub. No.: WO2018/033635
PCT Pub. Date: Feb. 22, 2018

(65) Prior Publication Data
US 2019/0284150 A1    Sep. 19, 2019

(30) Foreign Application Priority Data
Aug. 19, 2016  (NL) .................................... 2017340

(51) Int. Cl.
*C07D 307/06*    (2006.01)

(52) U.S. Cl.
CPC ................. *C07D 307/06* (2013.01)

(58) Field of Classification Search
CPC .................................................. C07D 307/06
USPC .......................................................... 549/509
See application file for complete search history.

(56) References Cited

U.S. PATENT DOCUMENTS

| | | | |
|---|---|---|---|
| 4,288,369 A | 9/1981 | Holy et al. | |
| 4,507,518 A | 3/1985 | Petrocine et al. | |
| 4,857,664 A * | 8/1989 | Huang | C07C 41/06 568/695 |
| 5,011,506 A * | 4/1991 | Harandi | C07C 41/06 44/447 |
| 5,102,428 A * | 4/1992 | Owen | C07C 1/20 44/446 |
| 5,154,801 A * | 10/1992 | Harandi | C07C 41/05 203/43 |
| 6,956,141 B1 | 10/2005 | Maas-Brunner et al. | |

FOREIGN PATENT DOCUMENTS

| | | | |
|---|---|---|---|
| CN | 1100049 C | * 1/2003 | .......... C07D 307/06 |
| DE | 700036 C | 12/1940 | |
| GB | 734431 | 8/1955 | |
| GB | 1 289 571 | 9/1972 | |
| JP | S60146836 A | 8/1985 | |

OTHER PUBLICATIONS

Yilmaz, Catal. Sci. Technol., 2013, 3, 2580.*
NL Search Report for corresponding priority Application No. NL 2017340, dated Nov. 16, 2016 Aug. 19, 2016 (11 pages).
PCT International Search Report for corresponding international Application No. PCT/EP2017/070961, dated Apr. 10, 2017 (2 pages).
PCT International Search Report and PCT Written Opinion for corresponding international Application No. PCT/EP20171070961, dated Oct. 4, 2017 (16 pages).
Olah, G A et al., "Synthetic Methods and Reactions: 99. Preparation of Cyclic Ethers Over Superacidic Perfluorinated Resinsulfonic Acid (NAFION-H) Catalyst", Synthesis, Georg Thieme Verlad, Stuttgart, DE, No. 6, Jun. 1, 1981, pp. 474-476 XP000569703.
Denney, Donald B. et al., "Cyclodehydration of 1,4-Butanediols by Pentaethoxyphosphorane," J. Org. Chem. 1984 49(15):2831-2832.
Gillis, Bernard T. et al., "Formation of Tetrahydrofuran Derivatives from 1,4-Diols in Dimethyl Sulfoxide," J. Org. Chem. 1963 28:1388-1390.
Kotkar, Dilip et al., "Cyclodehyration of Non-aromatic Diols on Al III-Montmorillonite Clay: Reactivity and Mechanism," J. Chem. Soc. Perkin Trans 1, 1988 p. 1749-1752.
Olah, George A. et al., Synthetic Methods and Reactions; 99 1. Preparation of Cyclic Ethers over Superacidic Perfluorinated Resinsulfonic Acid (Nafion-H) Catalyst, Sythesis, Jun. 1981 pp. 474-476.
Ren, Dezhang et al., "Production of 2,5-hexanedione and 3-methyl-2-cyclopenten-1-one from 5-hydroxymethylfurfural," Green Chem., 2016 18:3075-3081.
Sacia, Eric R. et al., "Synthesis of biomass-derived methylcyclopentane as a gasoline additive via aldol condensation/hydrodeoxygenation of 2,5-hexanedione," Green Chem., 2015 17:2393-2397.
Sherwood, James et al., "N-Butylpyrrolidinone as a dipolar aprotic solvent for organic synthesis," Green Chem., 2016 18:3990-3996.
Vlad, P.F. et al., "New Convenient Methods for the Preparation of Tetrahydofurans from 1,4-Diols," Synthesis, 1983 pp. 216-219.

(Continued)

*Primary Examiner* — Nizal S Chandrakumar
(74) *Attorney, Agent, or Firm* — Hoffman & Baron, LLP

(57) ABSTRACT

A process for the preparation of 2,2,5,5-tetramethyltetrahydrofuran (TMTHF) includes contacting a TMTHF precursor with a solid catalyst, where the TMTHF precursor is 2,5-dimethylhexane-2,5-diol and/or 2,5-dimethyl-4-hexen-2-ol, and where the solid catalyst is a beta zeolite. TMTHF produced by the process may be used as a solvent.

12 Claims, No Drawings

(56) References Cited

OTHER PUBLICATIONS

Office Action, Japanese Patent Application No. 530541/2019, dated Aug. 6, 2019.
Yamaguchi et al., "Cyclization of alkanediols in high-temperature liquid water with high-pressure carbon dioxide", Catalysis Today, 185 (2012); 302-305.

* cited by examiner

PREPARATION OF TMTHF

CROSS-REFERENCE TO RELATED APPLICATIONS

This application is the National Stage of International Application No. PCT/EP2017/070961, filed Aug. 18, 2017, which claims the benefit of Netherlands Application No. NL 2017340, filed Aug. 19, 2016, the contents of which is incorporated by reference herein.

TECHNICAL FIELD

The current invention relates to a process for the preparation of TMTHF, the use of a beta zeolite catalyst for the preparation of TMTHF, and the use of TMTHF as solvent, e.g. in a process for the polymerization of vinyl monomers.

BACKGROUND ART

Pressure is mounting in the EU to move away from many of the most popular solvents currently in use. Some are facing bans due to their toxicity, such as NMP, dichloromethane and toluene. Additionally, owing to recent international agreements to fight climate change, chemical companies are required to reduce $CO_2$ emissions for which solvents are a major contributor. This is due to the volumes in which they are used (up to 50% of the total mass of chemicals in the manufacture of active pharmaceutical ingredients), on top of the fact that they are sourced from petroleum and incinerated at the end of their lifetimes. In this way, carbon which has been stored in the earth's crust for millions of years as oil is converted to $CO_2$ and released to the atmosphere.

As biomass consumes $CO_2$ to grow, the use of solvents which have been sourced from biomass leads to no net increase in the levels of atmospheric $CO_2$, establishing a closed carbon cycle. In recent years, many bio-based solvents with diverse chemical, physical and solubility properties have been developed such as bio-ethanol, 2-methyltetrahydrofuran (2-MeTHF), dihydrolevoglucosenone (Cyrene®), para-cymene and some ionic liquids. However, bio-based low polarity, low boiling solvents which can potentially replace traditional hydrocarbon solvents such as toluene and hexane, are under-represented (see Sherwood et al. in Green Chem. 2016, 18, p 3990). While 2-MeTHF is a viable option for some applications, it is an ether, and like most commonly used ethers, forms explosive peroxides due to the presence of an easily extractable proton in the alpha-position to the ethereal oxygen. Hexamethyldisiloxane is another option, however its synthesis from biomass is not easy and upon combustion forms large quantities of ash.

This invention relates to the production of a non-peroxide-forming, low-boiling, low-polarity solvent that can potentially replace traditional hydrocarbon solvents such as toluene and hexane, and that can be produced from biomass (or in other words: is bio-based): 2,2,5,5-tetramethyltetrahydrofuran (TMTHF). TMTHF has a low boiling point of ~111° C. and low ETN value of 0.111, both comparable to toluene. Although TMTHF is an ether by definition as it contains an R—O—R' group (where R and R' are alkyl groups), it does not possess the peroxide-forming potential of other ethers such as THF or 2-MeTHF. This is due to the absence of a proton in the α-position relative to the ethereal oxygen. The α-proton in traditional ethers is readily removed by low energy light, forming radicals. Oxygen from the air can react with the radicals to form explosive peroxides. The rate of peroxide forming potential in ethers increases with increasing radical stability: primary α-carbon<<secondary α-carbon<tertiary α-carbon. As TMTHF does not contain any α-protons due to it containing two quaternary ethereal carbons, the potential to form peroxides is removed. The combination of these very favourable properties make TMTHF a rare low-boiling, low-polarity molecule which does not possess peroxide-forming potential and can be easily produced from biomass.

Methods of producing TMTHF from a precursor molecule comprising contacting the precursor with a catalyst have been reported in literature. Especially catalytic methods with 2,5-dimethylhexane-2,5-diol as a precursor have been described.

Denney et al. in J. Org. Chem. 1984, 49, p 2831 disclose a process for the preparation of TMTHF comprising contacting 2,5-dimethylhexane-2,5-diol with pentaethoxyphosphorane as a catalyst in DCM as a solvent.

Vlad & Ungur in Synthesis 1983, 1983, p 216 disclose a process for the preparation of TMTHF comprising contacting 2,5-dimethylhexane-2,5-diol with chlorotrimethylsilane as a catalyst in benzene as a solvent.

Gillis & Beck in J. Org. Chem. 1963, 28, p 1388 disclose a process for the preparation of TMTHF comprising contacting 2,5-dimethylhexane-2,5-diol with DMSO as both a solvent and catalyst.

Yamaguchi et al. in Catal. Today 2012, 185, p 302 disclose a process for the preparation of TMTHF comprising contacting 2,5-dimethylhexane-2,5-diol with hot liquid water in high pressure carbon dioxide as both catalyst and solvent.

Kotkar et al. in J. Chem. Soc. [Perkin 1] 1988, p 1749 disclose a process for the preparation of TMTHF comprising contacting 2,5-dimethylhexane-2,5-diol with aluminium-doped montmorillonite clay as a catalyst. A solvent was not used. However, the yield of the process was only 65%. As a matter of fact, in all aforementioned processes, TMTHF yields did not exceed 78%. A higher yield was achieved in solvent free processes.

DE700036C discloses a process for the preparation of TMTHF comprising contacting 2,5-dimethylhexane-2,5-diol with potassium pyrosulphate in absence of a solvent. The yield was 94.6%.

Olah et al. in Synthesis 1981, p 474 have used Nafion-H™ as a catalyst in the synthesis of TMTHF from 2,5-dimethylhexane-2,5-diol as a precursor. The advantage of a solid catalyst such as Nafion-H is that it can easily be separated from the reaction mixture. The synthesis had a yield of 94%. This leaves 6% for unreacted diol and side-products such as 2,5-dimethyl-2,4-hexadiene and 2,5-dimethyl-4-hexen-2-ol (see below).

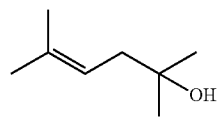

The side-products are difficult to separate from TMTHF. It is an objective of the invention to decrease the amount of side-products. It is another objective of the invention to increase the yield of TMTHF above 95%.

Nafion-H™ is a PTFE polymer which has been treated with sulfuric acid. It is very expensive to produce due to the high number of steps and energy required in its production. Furthermore, solid acid catalysts such as Nafion-H™ can become inactive over time. Some solid acid catalysts can be reactivated by calcination to remove organic material from the pores. This process cannot be done to Nafion-H™ due to its relatively low thermal stability, significantly lowering its reusability. Therefore, especially when large quantities of TMTHF need to be produced, the use of Nafion-H™ as a catalyst is disadvantageous. It is a further objective of the invention to provide a process for the preparation of TMTHF which utilizes a catalyst that is cheaper and/or easier to reactivate than Nafion-H™.

SUMMARY OF INVENTION

Thereto, the current invention provides a process for the preparation of 2,2,5,5-tetramethyltetrahydrofuran (TMTHF) comprising contacting a TMTHF precursor with a solid catalyst, wherein the TMTHF precursor is 2,5-dimethyl-hexane-2,5-diol and/or 2,5-dimethyl-4-hexen-2-ol, and wherein the solid catalyst is a beta zeolite.

DETAILED DESCRIPTION OF THE INVENTION

The invention may be illustrated by the following reaction scheme:

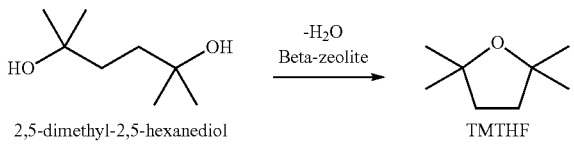

2,5-dimethyl-2,5-hexanediol          TMTHF

When 2,5-dimethylhexane-2,5-diol is contacted with a beta zeolite catalyst it is believed that 2,5-dimethyl-4-hexen-2-ol is produced as an intermediate before TMTHF is formed. The intermediate product may therefore be used instead or in combination with 2,5-dimethylhexane-2,5-diol.

Zeolites are microporous crystalline silica-alumina composites. The presence of aluminium atoms in the framework results in an overall negative charge on the surface of the material. Metal counterions such as $Ca^{2+}$ or $Mg^{2+}$ are present in the pores and they can be exchanged with protons to produce an acidic surface. Zeolites are prepared using templating agents, the nature of which determines the size of the pores. Beta-zeolites are prepared using tetraethylammonium cations as the templating agent while ZSM-5 zeolites are prepared using tetrapropylammonium cations as the templating agent. Adjusting the Si/Al ratio effects the acidity of the material: higher Si/Al ratios reduce the number of active sites within the catalyst but increase the number of stronger acid sites and the surface hydrophobicity.

Zeolites are very cheap and are the most used catalysts in the petrochemical industry along with sulfuric acid. Zeolites are much more robust than Nafion-H™, being able to take temperatures of over 1000° C. Zeolites can be reactivated simply by calcination to remove organic material from the pores.

Yields of 95% up to even 100% were obtained using beta-zeolites as a catalyst in a process according to the current invention. Other catalysts reported in the literature and/or tested by the current inventors were not as effective as beta-zeolites for the production of TMTHF. For example, ZSM-5 zeolite (Si/Al ratio 80:1) was much less effective with a yield of only 28%. In general, all other catalysts produced TMTHF in lower yields and with a high amount of a side product and some unreacted diol in the reaction mixture.

Preferably the beta zeolite has a Si/Al ratio of 150:1 or lower in respect of the amount of Si. Beta-zeolites with these Si/Al ratios have been found to perform excellently, producing TMTHF in yields of 95% and more.

More preferably, the beta zeolite catalyst has a Si/Al ratio of 30:1 or lower in respect of the amount of Si. Beta-zeolites with these Si/Al ratios (30:1 or lower, e.g. between 21-30) have been found to perform excellently, producing TMTHF in yields close to 100%.

Preferably the beta zeolite is beta-zeolite HCZB 25 and/or HBEA 25. A process according to the invention in which these particular beta zeolites were used as a catalyst produced TMTHF in a yield of 99-100%.

The TMTHF precursor may be in the liquid or gas phase. Preferably, contacting of the TMTHF precursor with a beta zeolite catalyst is carried out in a flow reactor packed with the beta zeolite catalyst. In such a reactor, liquid and gas phase reactions using a solid state catalyst are easily performed. Alternatively, contacting of the TMTHF precursor with a beta zeolite catalyst is carried out in a batch reactor.

Preferably the process is carried out at a temperature in the range of 50-200° C.

More preferably the process is carried out at a temperature in the range of 85-200° C. At a temperature of about 85° C., the 2,5-dimethylhexane-2,5-diol melts, and a solvent is not necessary for executing the process according to the invention. Most preferably the process is carried out at a temperature in the range of 100-175° C.

Preferably, the process is solvent free. Many of the aforementioned prior art methods required the use of a solvent, which is a disadvantage. Solvents need to be removed from the reaction product later, and increase the production costs.

The TMTHF precursor may be fully or partially petroleum derived. For example, 2,5-dimethyl-2,5-hexanediol can be produced according to the method of U.S. Pat. No. 6,956,141 B 1.

Preferably, the TMTHF precursor is bio-based. This is advantageous for the environment, as the use of solvents which have been sourced from biomass leads to no net increase in the levels of atmospheric $CO_2$, establishing a closed carbon cycle.

A TMTHF precursor obtained from fermentative biomass treatment processes can be used to make the TMTHF of the current invention. However, fermentative production of chemicals is expensive and susceptible to infection. To prevent infection, antibiotics can be used, although residual antibiotics in biorefinery side-streams can hinder their use as secondary feedstocks as the use of antibiotics can spread antibiotics resistance in microorganisms. It is another objective of the invention to overcome these disadvantages.

Thereto, preferably, the TMTHF precursor is obtained by a process which comprises chemocatalytic treatment of biomass. As such, chemocatalytic treatment of biomass is a more robust method of producing price sensitive chemicals such as solvents than the fermentative production.

Preferably, the TMTHF precursor is obtained from hydroxymethylfurfural (HMF). HMF is a bio-platform molecule produced by chemocatalytic treatment of biomass. HMF can be converted to 2,5-hexanedione (see Sacia et al. in Green Chem. 2015, 17, p 2393, and Ren et al. in Green Chem. 2016, 18, p 30'75). 2,5-hexanedione can be methylated at the carbonyl groups to produce 2,5-dimethyl-2,5-hexanediol.

The invention also provides for the use of a beta zeolite catalyst for the preparation of TMTHF, and the use of TMTHF prepared by a process according to the invention as solvent, e.g. in a process for the polymerization of vinyl monomers.

The present invention will be explained in more detail by reference to the following examples, but the invention should not be construed as being limited thereto.

EXAMPLES

Testing of several catalysts was performed as follows. 2,5-dimethylhexan-2,5-diol (5 g), a white solid, was added to a 25 ml round-bottomed flask and heated to 105° C. At ~85° C. the solid melts to a clear liquid. Upon reaching the desired temperature, 50 mg catalyst was added and the mixture was stirred for 1.5 hours. Yields and conversions were obtained by NMR and GC-FID of the organic phase. Results are summarized in table 1. Table 1 further includes catalyst results reported in the literature.

As can be seen yields of up from 95% were obtained using beta zeolites as a catalyst. Thus, beta zeolites outperform all other catalysts. Notably, yields are much higher than for another type of zeolite, ZSM-5. Moreover, even the 94% yield of Nafion-H™ is improved upon. Beta-zeolites HCZB 25 and HBEA 25 even performed excellently with a yield of 99-100%.

TABLE 1

Yields of TMTHF from 2,5-dimethylhexan-2,5-diol using different catalysts

| Catalyst | Yield | Conditions (reference) |
|---|---|---|
| Beta-zeolite HCZB 25 | 100.0 | As described above |
| Beta-zeolite HCZB 21 | 99.0 | As described above |
| Beta-zeolite HBEA 25 | 99.0 | As described above |
| Beta-zeolite HCZB 21 | 98.8 | As described above |
| Beta-zeolite HCZB 30 | 98.0 | As described above |
| Beta-zeolite HBEA 150 | 97.1 | As described above |
| Beta-zeolite HCZB 150 | 95.2 | As described above |
| Nafion-H ™ | 94.0 | 2 hrs, 130° C. (Olah et al.) |
| KSF 3 | 84.0 | As described above |
| Pentaethoxyphosphorane | 78.0 | 450 hrs, RT, DCM as solvent (Denney et al.) |
| DMSO, Chlorotrimethylsilane | 75.0 | 75 hrs, 20° C., benzene as solvent (Vlad & Ungur) |
| Al doped Montmorillonite | 65.0 | 175° C. (Kotkar et al.) |
| DMSO | 52.0 | 17 hrs, 162° C., DMSO as solvent (Gillis & Beck) |
| Carbonic acid | 40.0 | 3 hrs, 14.6 Mpa CO2 as solvent (Yamaguchi et al.) |
| ZSM-5 80 | 28.2 | As described above |
| SZ | 0.0 | As described above |

The invention claimed is:

1. A process for the preparation of 2,2,5,5-tetramethyltetrahydrofuran (TMTHF) comprises:
    contacting a TMTHF precursor with a solid catalyst,
    wherein the TMTHF precursor is 2,5-dimethylhexane-2,5-diol and/or 2,5-dimethyl-4-hexen-2-ol,
    wherein the process results in TMTHF containing less than 6% of unreacted precursor or side products,
    wherein the solid catalyst has a Si/Al ratio of 150:1 or lower in respect of the amount of Si, and
    wherein the solid catalyst is a beta zeolite selected from the group consisting of HCZB 25, HCZB 21, HCZB 30, HBEA 25, HCZB 150, HBEA 150, or combinations thereof.

2. The process according to claim 1, wherein the solid catalyst is beta-zeolite HCZB 25 and/or HBEA 25.

3. The process according to claim 1, wherein contacting of the TMTHF precursor with a solid catalyst is carried out continuously in a flow reactor packed with the solid catalyst.

4. The process according to claim 1, wherein contacting of the TMTHF precursor with a solid catalyst is carried out in a batch reactor.

5. The process according to claim 1, which is carried out at a temperature in the range of 50 to 200° C.

6. The process according to claim 5, which is carried out at a temperature in the range of 85 to 200° C.

7. The process according to claim 6, which is solvent free.

8. The process according to claim 1, wherein the TMTHF precursor is bio-based.

9. The process of claim 1, wherein the yield of TMTHF from 2,5-dimethylhexane-2,5-diol and/or 2,5-dimethyl-4-hexen-2-ol is greater than 95%.

10. The process according to claim 1, wherein the solid catalyst has a Si/Al ratio of 30:1 or lower in respect of the amount of Si.

11. The process according to claim 5, which is carried out at a temperature in the range of 100 to 175° C.

12. A process for the preparation of 2,2,5,5-tetramethyl-tetrahydrofuran (TMTHF) comprises:
    contacting a TMTHF precursor with a solid catalyst,
    wherein the TMTHF precursor is 2,5-dimethylhexane-2,5-diol and/or 2,5-dimethyl-4-hexen-2-ol, and
    wherein the solid catalyst is a beta zeolite selected from the group consisting of HCZB 25, HCZB 21, HCZB 30, HBEA 25, or combinations thereof,
    wherein the solid catalyst has a Si/Al ratio of 30:1 or lower in respect of the amount of Si, and
    wherein the yield of TMTHF from 2,5-dimethylhexane-2,5-diol and/or 2,5-dimethyl-4-hexen-2-ol is greater than 95%.

* * * * *